United States Patent [19]

Aubert et al.

[11] Patent Number: 5,185,159

[45] Date of Patent: Feb. 9, 1993

[54] PHARMACEUTICAL COMPOSITION BASED ON VALPROIC ACID AND A PROCESS FOR PREPARING IT

[75] Inventors: Daniel Aubert, Plaisance du Touch; Francis Blanc, Lattes; Henri Desmolin, Merignac; Michel Morre, Toulouse; Lucette Sindely, St. Andre de Cubzac, all of France

[73] Assignee: Sanofi, Paris, France

[21] Appl. No.: 654,027

[22] Filed: Feb. 12, 1991

Related U.S. Application Data

[60] Division of Ser. No. 313,304, Jan. 21, 1989, Pat. No. 5,017,613, which is a continuation of Ser. No. 4,303, Jan. 8, 1987, abandoned, which is a continuation of Ser. No. 631,602, Jul. 17, 1984, abandoned.

[30] Foreign Application Priority Data

Jul. 20, 1983 [FR] France .................................. 83 12375
Jul. 20, 1983 [FR] France .................................. 83 12376

[51] Int. Cl.$^5$ ................................................ A61K 9/14
[52] U.S. Cl. ..................................... 424/489; 424/469; 424/477; 424/482; 424/494

[58] Field of Search ................ 514/564, 547; 424/494, 424/477, 469, 482, 489; 530/363

[56] References Cited

U.S. PATENT DOCUMENTS

| 3,325,365 | 6/1967 | Hotko et al. | 424/489 |
| 4,316,884 | 2/1982 | Alam | 424/494 |
| 4,423,071 | 12/1983 | Chignac et al. | 514/547 |
| 4,442,124 | 4/1984 | Niklaus | 514/547 |
| 4,443,365 | 4/1984 | Sunahara et al. | 530/363 |
| 4,457,907 | 7/1984 | Porter | 424/477 |
| 4,606,909 | 8/1986 | Bechgaard | 424/469 |
| 4,699,927 | 10/1987 | Deboeck | 514/564 |
| 4,913,906 | 4/1990 | Friedman | 424/482 |

Primary Examiner—Thurman K. Page
Assistant Examiner—William E. Benston, Jr.
Attorney, Agent, or Firm—Wegner, Cantor, Mueller & Player

[57] ABSTRACT

New pharmaceutical composition based on valproic acid and one of the pharmaceutically acceptable salts thereof, obtained by a new galenic preparation process which makes it possible to improve and simplify the galenic production, this composition also containing excipients which favorably modify its kinetics and its bioavailability.

6 Claims, No Drawings

PHARMACEUTICAL COMPOSITION BASED ON VALPROIC ACID AND A PROCESS FOR PREPARING IT

This application is a divisional of Ser. No. 07/313,304, filed Jan. 21, 1989, now U.S. Pat. No. 5,017,613 which is a continuation of Ser. No. 07/004,303, filed Jan. 8, 1987, now abandoned, which is a continuation of Ser. No. 06/631,602, filed Jul. 17, 1984, now abandoned.

Dipropylacetic or valproic acid (D C I) of formula

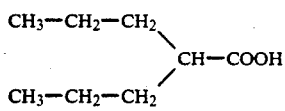

and sodium valproate are used in human therapy for their antiepileptic properties. Thus, sodium valproate is administered in different galenic forms such as drinkable solutions or tablets. It is known that, after oral administration, the bioavailability in the blood of valproic acid is nearly 100% and that the maximum concentration, which is rapidly reached, may cause side effects.

Moreover, the production of the tablets mentioned above has a number of disadvantages which it is felt should be mentioned:

1. granulation can only be carried out in the presence of a binder and with a wetting solvent;
2. before compression an adsorbent product and a lubricant must be added;
3. the core thus produced can only be given a coating which dissolves in the stomach if it has already been coated with an isolating lacquer;
4. the finished weight of the tablet is relatively great and the excipients represent approximately 40% of the total weight of the tablet;
5. all these operations have to be carried out in a dehydrated atmosphere with a relative humidity of 30%.

The present invention relates to new pharmaceutical compositions which can be administered by oral route and which contain a mixture of valproic acid and one of the pharmaceutically acceptable salts thereof.

It relates more particularly to the preparation of tablets the final weight of which is significantly less than that obtained by the conventional methods of galenic preparation.

The applicants have also discovered that the use, in the same tablet, of valproic acid combined with one of the pharmaceutically acceptable salts thereof and of a delaying excipient has the unexpected advantage of preventing the maximum blood concentration of the active principle from causing side effects (resulting from the substantial increase in the concentration of free valproic acid), whilst maintaining a blood concentration which is useful in terms of a delayed action; it also has the advantage of unexpectedly improving the process for producing the tablet and thus avoiding the various galenic disadvantages mentioned hereinbefore.

The invention thus relates to the production of pharmaceutical specialities which satisfy the above criteria.

In fact, pharmaceutical specialities are available on the market in France, containing either 200 mg or 500 mg of sodium valproate per dosage unit, the excipient used consisting of calcium silicate excipient, polyvidone excipient, magnesium stearate, talc, polyoxyethylene glycol 400, corn starch, titanium oxide, yellow iron oxide, cellulose acetophthalate and diethylphthalate, the finished weight being, for example, 800 mg in the case of the coated tablet containing 500 mg of sodium valproate, corresponding to 434 mg of valproic acid.

The processes for producing specialities based on valproic acid or one of the pharmaceutically acceptable salts thereof all use the stage of granulation carried out with a binder such as polyvidone excipient and a wetting solvent such as isopropyl alcohol or water. An absorbent product such as calcium silicate excipient and a lubricant such as magnesium stearate are added to the resulting granules before compression; after compression, the core thus produced is given an isolating coating consisting of polyvidone or methacrylate and then, if desired, an enteric release coating. Thus, the core has a weight of 562.5 mg and the isolating layer and the coating have a weight of 237.5 mg, giving a final weight of 800 mg.

It was thus thought necessary to improve the processes for preparing these pharmaceutical specialities so as to obtain a finished weight for the tablet of less than 800 mg, whilst retaining the same quantity of active principle expressed as valproic acid and the same characteristics of bioavailability.

The invention thus relates to the production of a speciality which has the above characteristics but in which the methods of production are simplified and improved.

Thus, the granules for compression are formed directly by simply mixing suitable proportions of valproic acid and one of the pharmaceutically acceptable salts thereof in the absence of any binder or granulating solvent. In fact, valproic acid is added slowly, either directly or by spraying, to the valproic acid salt; the granular agglomeration occurs automatically in a few minutes and the granules thus obtained are passed through a screen for calibration. This operation may be carried out in an atmosphere of 55-60% relative humidity, without the risk of any uptake of moisture.

The compressibility of these granules is very good and moreover the valproic acid acts as a lubricant. To avoid any tendency to stick to the punch, it was found necessary to add precipitated silica to the granules before compression.

Another advantage of the invention is the possibility of directly applying any coating, including an enteric coating, to the core, thus doing away with the nuisance and time spent on applying the isolating layer.

In other words, the advantages of the invention are granulation by simply mixing valproic acid and one of the pharmaceutically acceptable salts thereof, without any solvent and hence without any drying a simplified formula a lower core weight no need to work in a dehydrated atmosphere with a relative humidity of 30% a less hygroscopic core a lower end weight for the tablet.

A process carried out at ambient temperature for producing the tablets according to the invention is described in detail hereinafter, as a non-restrictive example; the proportions given relate to 1000 tablets: 145 g of valproic acid, in liquid form, are added slowly or sprayed on to 333 g of sodium valproate, which is in powder form; after the rapid formation of a granular agglomeration, the granules are passed through a screen in order to calibrate them.

52 g of precipitated silica are added to the granules before compression and then the mixture is compressed The cores thus obtained each weigh 530 mg, valproic acid constitutes 30.33% of the active principle and sodium valproate is 69.67% of the active principle; expressed as valproic acid, each tablet contains 434 mg corresponding to 500 mg of sodium valproate. These tablets are lacquered for example using hydroxypropyl-methyl cellulose (18 mg/tablet) and glycerol (7 mg/tablet) or any other suitable lacquer.

The production of these tablets according to the invention may be shown diagrammatically as follows, the quantities given corresponding to the production of 1000 tablets.

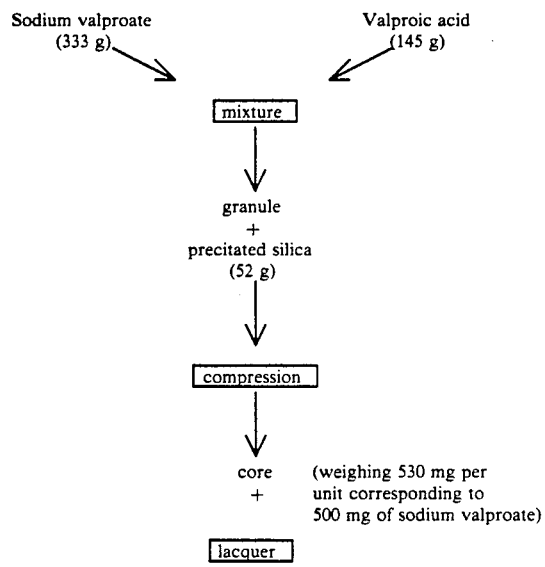

Various tests were carried out in which the proportions of valproic acid and sodium valproate were varied and suitable results were obtained with mixtures containing between 15 and 48% of valproic acid and between 85 and 52% of sodium valproate. Similarly, the behaviour in moisture of the mixture of sodium valproate and valproic acid showed that, after 14 days of contact with 55% relative humidity, the mixture containing 10% of valproic acid and 90% of sodium valproate had taken up 22% of moisture, the mixture containing 20% of valproic acid and 80% of sodium valproate had taken up 9% of moisture, whereas the mixture containing 30% of valproic acid and 70% of sodium valproate had taken up virtually no moisture.

However, it should be pointed out that it is always possible to add various conventional excipients during production of the core, depending on the equipment used and the operating conditions. These additives, which constitute a small percentage, will not modify the characteristics of bioavailability of the medicament of the invention described above.

As has already been pointed out, tests on comparative bioavailability were carried out with standard commercial tablets containing 500 mg of sodium valproate and the tablets according to the invention which also contained 500 mg of sodium valproate (or 434 mg of valproic acid).

Six healthy volunteers aged 24 to 30 were each given a single dose of two tablets corresponding to 1000 mg of sodium valproate or 868 mg of valproic acid; the tablet was given with a glass of water after the volunteers had fasted and the first meal, which was low in lipids, was given about 4 hours after the tablets were taken The commercial product and the medicament of the invention were given successively with a rest period of at least 8 days between two sequences.

Blood samples were taken at the following times: 0.10 min, 30 min, 45 min, 1 h, 1 h 30, 2 h, 2 h 30, 3 h, 3 h 30, 4 h, 4 h 30, 5 h, 6 h and 8 h, the time 0 corresponding to the first appearance of traces of valproic acid in the plasma.

The plasma was separated by centrifuging at 3000 rpm for a period of 5 minutes and then frozen until required for analysis.

The valproic acid was titrated in the samples by gas-liquid chromatography using flame ionisation detection in a Hewlett - Packard 5710 A apparatus fitted with an HP 7672 A automatic injector.

50 μg of sodium 1-methyl-cyclohexyl-carboxylate (internal standard) and 0.100 ml of 0.5N hydrochloric acid were added to 0.5 ml of plasma. The valproic acid and the internal standard were extracted with 0.5 ml of chloroform by vortex agitation for 1 minute and then centrifuging for 15 minutes at 6000 rpm. A calibration range was prepared in exactly the same way in the plasma.

The average plasma concentrations of valproic acid expressed as μg/ml as a function of time are shown in the following table:

| | Products | |
|---|---|---|
| Time | Standard commercial medicament (batch A) | Medicament according to the invention (batch B) |
| 0 | ε | ε |
| 10 mn | 45 | 47 |
| 30 mn | 90 | 86 |
| 45 mn | 97 | 95 |
| 1 h | 89 | 86 |
| 1 h 30 | 87 | 85 |
| 2 h | 85 | 82 |
| 2 h 30 | 74 | 71 |
| 3 h | 70 | 68 |
| 3 h 30 | 65 | 63 |
| 4 h | 62 | 60 |
| 4 h 30 | 57 | 59 |
| 5 h | 55 | 54 |
| 6 h | 51 | 50 |
| 8 h | 45 | 46 |

The results obtained indicate the following points:

1. the bioavailability of the commercial product and of the medicament according to the invention are substantially the same;

2. the maximum concentration is, after a period of 45 minutes, 97 μg/ml for a batch A and 95 μg/ml for batch B;

3. the areas under the curves are substantially identical for both batches:
940±75 for batch A
949±80 for batch B These results confirm that the production of the tablets according to the process of the invention does not alter the bioavailability of the active principle as existed with the commercially available product.

As has been pointed out hereinbefore, the applicants have also discovered that the use, in the same tablet, of valproic acid combined with one of the pharmaceutically acceptable salts thereof and of a delaying excipient has the unexpected advantage of preventing the maximum blood concentration of the active principle from causing side effects, whilst prolonging this blood concentration, within the scope of a delayed action, within the range of therapeutic concentrations.

The granules for compression are formed directly by simple mixing of suitable proportions of valproic acid to which ethyl cellulose has been added and one of the pharmaceutically acceptable salts thereof which may or may not contain eudragit, in the absence of any binder or any granulating solvent. The mixture of valproic acid and ethyl cellulose is added slowly to the mixture of valproic acid salt and eudragit; the granular agglomeration is formed automatically in a few minutes and the granules thus obtained are passed through a screen for calibration. This operation may be carried out in an atmosphere of 55 to 60% relative humidity without any danger of absorption of moisture.

In order to avoid any tendency to stick to the punch, it was found necessary to add precipitated silica to the granules before compression.

A process carried out at ambient temperature for producing the tablets according to the invention is described in detail hereinafter, as a non-restrictive example; the proportions given refer to 1000 tablets: 145 g of valproic acid together with 12 g of ethyl cellulose are added slowly to the mixture consisting of 333 g of sodium valproate and 113 g of eudragit; after the rapid formation of a granular agglomeration, the granules are passed through a screen for calibration. 52 g of precipitated silica are added to the granules before compression and then the mixture is compressed. The cores thus obtained each weigh 655 mg and are coated, for example, with 18 mg of hydroxypropymethyl cellulose and 7 mg of glycerol or any other suitable lacquer; the tablet C is obtained which corresponds to 500 mg of sodium valproate (or 434 mg expressed as valproic acid).

In another variant of the invention, no eudragit is added to the 333 g of sodium valproate. All the operations of production are carried out in the same way, but the weight of each core is then 542 mg and the coated tablet weighs 567 mg; a tablet B is obtained which corresponds to 500 mg of sodium valproate.

Other variants of the invention consist in modifying the respective quantities of ethyl cellulose (from 5 to 125 mg per dosage unit) and eudragit (from 50 to 150 mg per dosage unit) depending on the desired "delaying effect" and dispensing with an enteric coating on the core.

The production of the tablets according to the invention may be diagrammatically shown as follows:

Tablet C

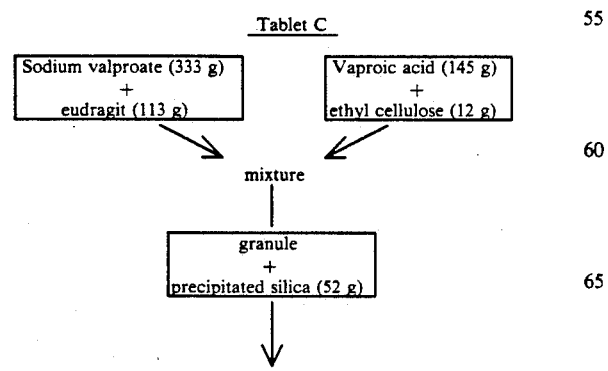

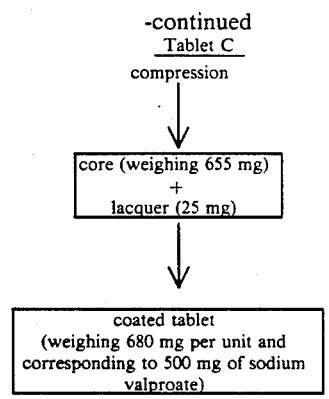

Tablet D:

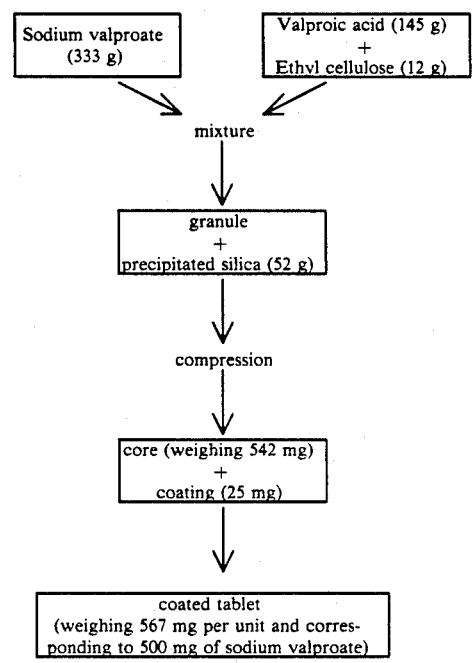

In order to demonstrate the delaying effect of the medicament according to the invention, dissolution tests were carried out in vitro and bioavailability tests were carried out in vivo, the control tablet T having been produced in the same way but containing no ethyl cellulose nor eudragit. The production of the tablet T can be diagrammatically shown as follows:

Tablet T:

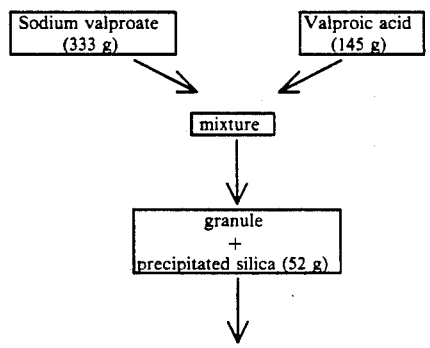

-continued

Tablet T:

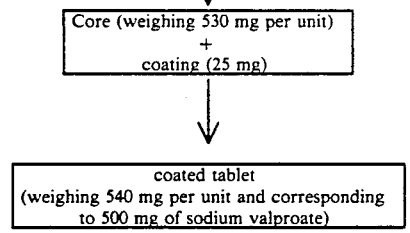

In Vitro Tests (Dissolution Test)

The dissolution test which was carried out was intended to determine the quantity of free valproic acid which went into solution in an artificial medium with a phosphate buffer at pH 6.8, the quantity of active principle being determined by titration in samples taken from the dissolution medium at various predetermined intervals of time.

The test was carried out using the technique described in Technical Note No. 79 (Pro-Pharmacopoea (Bull. Ordre Pharm, March 1980, no. 231).

The results obtained are shown in the following table. They are expressed as percent based on the quantity of valproic acid (434 mg) contained in each dosage unit.

|  | Products | | |
|---|---|---|---|
| Time | Tablet T | Tablet C | Tablet D |
| 0 | 0 | 0 | 0 |
| 30 mn | 60 | 24 | 38 |
| 1 h | 83 | 31 | 49 |
| 1 h 30 | 90 | 35 | 61 |
| 2 h | 95 | 40 | 68 |
| 2 h 30 | 97 | 43 | 73 |
| 3 h | 101 | 45 | 79 |
| 3 h 30 | 102 | 48 | 83 |
| 4 h | 103 | 50 | 87 |
| 4 h 30 | 103 | 53 | 88 |
| 5 h | 103 | 56 | 90 |
| 5 h 30 | 103 | 58 | 93 |
| 6 h | 103 | 60 | 95 |

In Vivo Tests (Bioavailability)

The tests on comparative bioavailability were carried out with the tablets T, tablets C and tablets D, each of these tablets containing 500 mg of sodium valproate.

Six healthy volunteers aged 24 to 30 were each given a single dose of two tablets corresponding to 1000 mg of sodium valproate or 868 mg of valproic acid; the tablets were accompanied by a glass of water after the volunteer had fasted and the first meal, which was low in lipids, was given about 4 hours after the tablet was taken. The tablets C, D and T were given successively with a rest period of at least eight days between the two sequences.

The blood measurements were taken at the following times: 0.10 min, 30 min, 45 min, 1 h, 1 h 30, 2 h, 2 h 30, 3 h, 3 h 30, 4 h, 4 h 30, 5 h, 6 h and 8 h, the time 0 corresponding to the first appearance of traces of valproic acid in the plasma.

The method of extraction and blood titration of the valproic acid are identical to those described above.

The average plasma concentrations of valproic acid expressed in $\mu$g/ml as a function of time are shown in the following table:

|  | Products | | |
|---|---|---|---|
| Time | Tablet T | Tablet C | Tablet D |
| 0 | $\epsilon$ | $\epsilon$ | $\epsilon$ |
| 10 mn | 47 | 15 | 22 |
| 30 mn | 86 | 24 | 38 |
| 45 mn | 95 | 29 | 44 |
| 1 h | 86 | 35 | 49 |
| 1 h 30 | 85 | 46 | 57 |
| 2 h | 82 | 55 | 69 |
| 2 h 30 | 71 | 58 | 70 |
| 3 h | 68 | 60 | 70 |
| 3 h 30 | 63 | 63 | 69 |
| 4 h | 60 | 65 | 67 |
| 4 h 30 | 59 | 67 | 65 |
| 5 h | 54 | 69 | 65 |
| 6 h | 50 | 73 | 63 |
| 8 h | 46 | 65 | 59 |

The following findings are obtained from the in vitro and in vivo results:

1. the dissolution tests are in favour of the delaying effect of the tablets C and D compared with the tablets T;

2. The bioavailability tests confirm the results obtained in vitro, namely that, compared with the tablets T, the tablets C and D have the characteristics of a delaying effect; in fact, the formulation of the medicament of the invention unexpectedly and favourably modifies the bioavailability of valproic acid (tablets C and D); this change in the bioavailability makes it possible to avoid the side effects caused by the sudden introduction of valproic acid into the circulation (tablet T); the maximum concentration is obtained after 45 minutes at 95 $\mu$g/ml for batch T, after 6 hours at 73 $\mu$g/ml for batch C and after 2 hours 30 minutes to 3 hours at 70 $\mu$g/ml for batch D.

These results therefore confirm the delaying effect of the medicament of the invention which makes it possible to flatten the bioavailability curve and hence to avoid the side effects of the sudden introduction of valproic acid into the circulation and also to avoid any major differences between the maximum and minimum concentrations which make the level of valproicaemia at any time during repeated administration very haphazard.

Other tests have been carried out in man by oral administration of a single dose of 1000 mg of sodium valproate either in the form of a drinkable solution, solution E, or in the form of tablets according to the invention according to formula C with a delayed action Additional tests were carried out on tablets of formula C by administering two tablets in a single dose per day for 8 days corresponding to a daily dose of 1000 mg of sodium valproate. The tests were carried out on 8 healthy volunteers according to the plan described above (the curves obtained are shown in the accompanying single drawing):

1) After Single Administration

The pharmacokinetic parameters determined were:

C max : maximum plasma concentration observed, expressed in $\mu$g/ml$^{-1}$.

T max : time taken to reach the C max, expressed in hours after administration of the product AUC$_0$: area under the curve of the plasma concentrations of valproic acid as a function of time, expressed in μg.h.ml$^{-1}$.

| Form | Parameter | | |
|---|---|---|---|
| | C max | T max | AUC$_0^\infty$ |
| solution E | 90.2 ± 3.3 | 0.4 ± 0.1 | 1330 ± 117 |
| tablet C | 50.5 ± 3.6 | 9.1 ± 0.8 | 1592 ± 129 |

A study of this table shows
a slowing down of the speed of availability of the valproic acid from tablet C according to the invention.
A greater quantity of active principle which is bioavailable after administration of the medicament according to the invention, explained by a reduced coating of enzymes.

2) After Administration for 8 Days:

The pharmacokinetic parameters determined were:
Values of the Cmin in the steady state were calculated from the values of the minimum plasma concentrations obtained before administration on days $J_{19}$, $J_{20}$ and $J_{21}$ and 24 hours after the last administration on $J_{21}$.
For all the 8 volunteers studied, the average is 42.6±4.6 μg.ml$^{-1}$.

Speed of Passage

The average values of the parameters of the maximum plasma concentration and Tmax obtained after the last administration were 77.2±5.8 μg.ml$^{-1}$ and 6.9±0.9 h, respectively.

Area Under the Curve in the Interval τ Between Two Administrations

The values below show that on repeated administration and when a state of equilibrium is attained, the intensity of passage of the active principle is comparable to that which was calculated between the time 0 and infinity during a single dosage:

$$\overline{AUC_{\tau n}^{\tau n+1}} \; 1\,501 \pm 126$$

$$\overline{AUC_0^\infty} = 1\,592 \pm 129$$

Kinetics of Elimination

It was interesting to note that, when the repeated administration was stopped, the kinetics of elimination of the medicament were hardly altered compared with that which followed the first administration.

$\beta = 0.036 \pm 0.003$ h$^{-1}$ after the last dosage $\beta = 0.040 \pm 0.003$ h$^{-1}$ after the first dosage 3) On studying the results obtained, it was found that:
3.1. After oral administration of a single dose in man, the speed of entry of the valproic acid into the general circulation from the tablets according to the invention is significantly slower than a form with immediate release (solution E).
With the same dosage of active principle, the quantity of valproic acid which is bioavailable is about 20% greater when the tablets according to the invention are administered.
The kinetics described by the medicament of the invention correspond to the objective sought: flattening of the plasma peak, bioavailability which is at least equal and possibly improved: these criteria correspond perfectly to the definition of a controlled release form.
3.2. A study of the bioavailability of the tablets according to the invention was expanded to include tests on chronic administration. A dose equivalent to 1000 mg of sodium valproate was administered in a single dosage per 24 hours until a state of equilibrium was obtained The kinetics after the last dosage are linear under the experimental conditions described.
The controlled release form makes it possible to prolong the period of presence in the plasma within the range of the effective concentrations without reaching the high concentrations which are responsible for intolerance Moreover, it makes it possible to reduce substantially the habitually considerable differences between the maximum and minimum concentrations which make the level of valproicaemia at any moment during repeated administration very haphazard.
Thus, the tablets according to the invention satisfy the aims of the invention and are favourable in terms of therapeutic use.

We claim:
1. An orally administrable controlled release tablet pharmaceutical composition comprising a ratio of about one mole of valproic acid to about two moles of sodium valproate and a carrier for controlled release, wherein said tablet is produced without the addition of binder or granulating solvent.
2. The pharmaceutical composition of claim 1 wherein the carrier is polymeric methacrylate.
3. The pharmaceutical composition of claim 1 wherein the carrier is ethyl cellulose.
4. The pharmaceutical composition of claim 1 wherein the carrier comprises ethyl cellulose and polymeric methacrylate.
5. The pharmaceutical composition of claim 1 wherein the carrier comprises ethyl cellulose and polymeric methacrylate, further comprising an anti-sticking amount of precipitated silica.
6. The pharmaceutical composition of claim 5 coated with an enteric coating.

* * * * *